(12) United States Patent
Zeng et al.

(10) Patent No.: US 9,903,002 B2
(45) Date of Patent: Feb. 27, 2018

(54) **NON-CODING RNA OF *SALMONELLA* AND IDENTIFICATION AND USE THEREOF**

(71) Applicant: JIANGSU MICROMEDMARK BIOTECH CO. LTD., Jiangsu (CN)

(72) Inventors: Ke Zeng, Beijing (CN); Hongwei Gu, Beijing (CN); Chenyu Zhang, Beijing (CN); Tianfu Zhang, Beijing (CN)

(73) Assignee: JIANGSU MICROMEDMARK BIOTECH CO., LTD., Taizhou, Jiangsu (CN)

( * ) Notice: Subject to any disclaimer, the term of this patent is extended or adjusted under 35 U.S.C. 154(b) by 0 days.

(21) Appl. No.: 15/103,288

(22) PCT Filed: Dec. 9, 2014

(86) PCT No.: PCT/CN2014/093385
§ 371 (c)(1),
(2) Date: Jun. 9, 2016

(87) PCT Pub. No.: WO2015/085905
PCT Pub. Date: Jun. 18, 2015

(65) Prior Publication Data
US 2016/0319332 A1    Nov. 3, 2016

(30) Foreign Application Priority Data
Dec. 9, 2013   (CN) .......................... 2013 1 0665565

(51) Int. Cl.
*A61K 48/00* (2006.01)
*C12N 15/11* (2006.01)
(Continued)

(52) U.S. Cl.
CPC ............ *C12Q 1/689* (2013.01); *C12N 15/113* (2013.01); *C12N 2310/113* (2013.01);
(Continued)

(58) Field of Classification Search
USPC ..................................... 536/23.1, 24.3, 24.5
See application file for complete search history.

(56) References Cited

FOREIGN PATENT DOCUMENTS

| CN | 102149826 A | 8/2011 |
|---|---|---|
| EP | 2135947 A1 | 12/2009 |

(Continued)

OTHER PUBLICATIONS

Cao, Xuesong et al., "Analysis of Regulation Role of sRNA (istR) in *Salmonella* Resistant to Reactive Nitrogen and Oxygen Intermediates," Microbiology China Aug. 20, 2011, pp. 1241-1248.
(Continued)

*Primary Examiner* — Terra C Gibbs
(74) *Attorney, Agent, or Firm* — Rothwell, Figg, Ernst & Manbeck, p.c.

(57) ABSTRACT

The present invention provides *Salmonella* non-coding RNA and the identification and application thereof. In particular, the present invention proves through experiments that a *Salmonella* bacterium delivers non-coding RNAs (ncRNAs) encoded by the bacterium itself into a host cell, generates milRNAs similar to microRNAs by means of a microRNA splicing system in the cell, regulates the immune system with the milRNAs, and further protects the *Salmonella* bacterium from being cleared by the host. Adsorbing milRNAs using milRNA inhibitors can effectively inhibit the survival ability of the bacterium in the cell, leading to a reduced vitality of the bacterium. The present invention further provides relevant reagents and methods for effective detection of, treatment to and study on *Salmonella* bacteria or *Salmonella* infectious diseases.

4 Claims, 5 Drawing Sheets

(51) Int. Cl.
*C12Q 1/68* (2018.01)
*C12N 15/113* (2010.01)

(52) U.S. Cl.
CPC ............... *C12N 2310/3231* (2013.01); *C12Q 2600/136* (2013.01); *C12Q 2600/158* (2013.01); *C12Q 2600/178* (2013.01)

(56) References Cited

FOREIGN PATENT DOCUMENTS

| | | |
|---|---|---|
| WO | 2007084488 A3 | 11/2007 |
| WO | 2009137505 A2 | 11/2009 |

OTHER PUBLICATIONS

Xiao, Biu, "Screening and Identification of Small Non-Coding RNAs in H.pylori and the Negative Regulatory Role of MiRNAs in the Inflammatory Response during H.pylori Infection," PhD thesis of Third Military Medical University, May 15, 2010.

Papenfort, Kai et al., "σE-dependent Small RNAs of *Salmonella* Respond to Membrane Sites by Accelerating Global Omp mRNA Decay," Molecular Microbiology, vol. 62, No. 6, Dec. 31, 2006, pp. 1674-1688.

Foster, N. et al., "Inhibition of IFN-γ-Stimulated Proinflammatory Cytokines by Vasoactive Intestinal Peptide (VIP) Correlates with Increased Survival of *Salmonella enterica* Serovar Typhimurium PhoP in Murine Macrophages," Journal of Interferon & Cytokine Research, vol. 25, Dec. 31, 2005, pp. 31-42.S.

International Search Report dated Jan. 20, 2015, 8 pages.

SEQUENCE LISTING

```
<160> NUMBER OF SEQ ID NOS: 11

<210> SEQ ID NO 1
<211> LENGTH: 24
<212> TYPE: RNA
<213> ORGANISM: Salmonella

<400> SEQUENCE: 1
ugugggcacu cgaagauacg gauu                                              24

<210> SEQ ID NO 2
<211> LENGTH: 27
<212> TYPE: RNA
<213> ORGANISM: Salmonella

<400> SEQUENCE: 2
augcgagagu agggaacugc caggcau                                           27

<210> SEQ ID NO 3
<211> LENGTH: 28
<212> TYPE: RNA
<213> ORGANISM: Salmonella

<400> SEQUENCE: 3
uccucuguag uucagucggu agaacggc                                          28

<210> SEQ ID NO 4
<211> LENGTH: 23
<212> TYPE: RNA
<213> ORGANISM: Salmonella

<400> SEQUENCE: 4
gaagguggcg gaauugguag acg                                               23

<210> SEQ ID NO 5
<211> LENGTH: 21
<212> TYPE: RNA
<213> ORGANISM: Salmonella

<400> SEQUENCE: 5
gcccggaugg uggaaucggu a                                                 21

<210> SEQ ID NO 6
<211> LENGTH: 74
<212> TYPE: DNA
<213> ORGANISM: Artificial
<220> FEATURE:
<223> OTHER INFORMATION: Oligonucleotide
```

```
<400> SEQUENCE: 6
tgtgggcact cgaagatacg gattcttaac gtcctaggac gaaaaatgaa taccaagtct    60
caagagtgaa cacg                                                     74

<210> SEQ ID NO 7
<211> LENGTH: 24
<212> TYPE: RNA
<213> ORGANISM: Artificial
<220> FEATURE:
<223> OTHER INFORMATION: Oligonucleotide

<400> SEQUENCE: 7
aauccguauc uucgagugcc caca                                          24

<210> SEQ ID NO 8
<211> LENGTH: 27
<212> TYPE: RNA
<213> ORGANISM: Artificial
<220> FEATURE:
<223> OTHER INFORMATION: Oligonucleotide

<400> SEQUENCE: 8
augccuggca guucccuacu cucgcau                                       27

<210> SEQ ID NO 9
<211> LENGTH: 28
<212> TYPE: RNA
<213> ORGANISM: Artificial
<220> FEATURE:
<223> OTHER INFORMATION: Oligonucleotide

<400> SEQUENCE: 9
gccguucuac cgacugaacu acagagga                                      28

<210> SEQ ID NO 10
<211> LENGTH: 23
<212> TYPE: RNA
<213> ORGANISM: Artificial
<220> FEATURE:
<223> OTHER INFORMATION: Oligonucleotide

<400> SEQUENCE: 10
cgucuaccaa uuccgccacc uuc                                           23

<210> SEQ ID NO 11
<211> LENGTH: 21
<212> TYPE: RNA
<213> ORGANISM: Artificial
<220> FEATURE:
<223> OTHER INFORMATION: Oligonucleotide

<400> SEQUENCE: 11
uaccgauucc accauccggg c                                             21
```

NON-CODING RNA OF *SALMONELLA* AND IDENTIFICATION AND USE THEREOF

CROSS-REFERENCE TO RELATED APPLICATIONS

The present application is a national stage filing under 35 U.S.C. § 371 of National Phase Entry of PCT/CN2014/093385, filed on 9 Dec. 2014, which in turn claims priority to Chinese Patent Application No. CN 20130665565.7, filed on 9 Dec. 2013. The disclosures of each of the above applications are hereby incorporated by reference in their entireties into the present application.

TECHNICAL FIELD

The present invention relates to the field of biotechnology, more particularly to *Salmonella* non-coding RNA and the identification and application thereof.

BACKGROUND ART

Microorganism is a general term of tiny organisms which are widely distributed in nature, are not visible to the naked eyes but can be observed only after being magnified at hundreds of times, thousands of times or even tens of thousands of times under an optical microscope or an electron microscope. Their characteristics include a tiny size, a simple structure, rapid reproduction, easy variation and strong adaptive capacity to environment.

Microorganisms are of wide varieties, and are extremely widely distributed in nature. A variety of microorganisms are also present on body surfaces and cavities communicated with exterior of human, animals and plants.

One of the most important influences of microorganisms on human is to cause some diseases, especially infectious diseases. Although the human has made great progress in the prevention and treatment of diseases, newly occurring and recurring microbial infections continue to occur, and many diseases are lack of effective therapeutic drugs all the time. Furthermore, the wide abuse of broad-spectrum antibiotics causes a strong selection pressure, so that many strains mutate, resulting in more dangerous drug-resistant strains.

All microorganisms growing on or in a living body are called parasitic microorganisms, and the microorganisms in parasitic make a living through depriving nutrition of other organisms, even depending on some parts of the bodies of other organisms as nutrients. Microorganisms can enter a human or animal body through the mouth, skin or respiratory tract, and grow and reproduce by using the nutrition of the human or animal body. If these bacteria produce toxins, the host will fall ill, such as of cholera, typhoid and pneumonia. Diseases such as AIDS and common cold are caused by viruses. Viruses are comparatively more specific parasitic microorganisms; because they cannot live outside of living cells, they are called strictly parasitic microorganisms.

Microbial infections are common clinical diseases caused by microorganisms. For the diagnosis of most of bacterial diseases, bacteriological diagnosis is required in order to determine the causes of diseases. However, isolating bacteria from a specimen does not necessarily mean that this bacterial species is the pathogen of the disease, and thus a comprehensive analysis shall be performed according to the clinical situation of the patient, the specimen collection site, and the species of the acquired bacteria. Sometimes virulence, cell and animal tests shall be made to determine pathogenicity of the strain.

Since bacteria and their metabolites have antigenicity, bacterial infections can also be diagnosed by detecting antibodies. Furthermore, gene diagnosis, a new method for diagnosing bacteria by detecting genetic materials of bacteria, is developed in recent years. However, the detection method mentioned above requires tedious operation and strict sample collection and preservation conditions, but also has a high false positive rate in the test results and a long detection period, which could easily lead to delay of the patient's treatment.

An infectious disease, especially a chronic persistent infection, is one of global stubborn diseases harmful to the human health and life. Intracellular pathogens that pose significant impact on human include *Mycobacterium tuberculosis, Salmonella, Brucella, Legionella pneumophila, Listeria*, and *Mycobacterium leprea*. Seven diseases, including tuberculosis, AIDS and hepatitis, form global threats, and the reason why they are difficult to treat is closely related to the intracellular parasitism of pathogens.

It is a difficult problem to treat intracellular microbial infections. The main reason includes: when the pathogens invade and lie dormant in the cells, it is difficult to deliver a conventional antibiotic to the cells where the pathogens hide, and even if delivered, it is difficult to achieve an effective microbicidal effect at the concentration of antibiotic; antibodies could hardly enter the cells to play a role; and after the intracellular bacteria are successfully living in cells, they could not only escape from the immune phagocytosis, killing and clearance, but also exist for a long time in the cells and lead to disease of the body at the appropriate time (e.g., when immunity of the body decreases).

*Salmonella* is a large group of Gram-negative bacilli which live in the human and animal intestinal tracts and have similar biochemical reactions and antigen structures, of which some are specifically pathogenic to humans, some are only pathogenic to animals, and some are pathogenic to both humans and animals, which are collectively referred to as *Salmonella*. Not less than 1800 kinds of *Salmonella* have now been found, and are divided into A, B, C, D, E and other basic bacterial types depending on the antigen constituents. The strains relevant to human diseases mainly include paratyphoid A bacilli in group A, paratyphoid B bacilli and *Salmonella typhimurium* in group B, paratyphoid C bacilli and *Salmonella cholerae* in group C, and *Salmonella typhi* and *Salmonella enteritidis* in group D. The bacteria may cause fowl typhoid, pullorum disease, cholera hog, *Salmonella typhimurium* disease, swine paratyphoid, Equi *salmonellosis* disease and other diseases. *Salmonella cholerae* has the strongest pathogenicity, and then are *Salmonella typhimurium* and *Salmonella enteritidis*. *Salmonella* infections or eating foods contaminated with faeces of carriers may induce food poisoning.

Therefore, in order to control microbial infectious diseases, there is an urgent need to develop new diagnostic and therapeutic techniques with simple operation and accurate results so as to improve the laboratory diagnosis and clinical treatment of such diseases to avoid delays of the patient's condition and reduce the physical and economic burden of patients.

CONTENTS OF THE INVENTION

An object of the present invention is to provide a diagnostic and therapeutic method for microbial infections with simple operation and accurate results.

In the first aspect of the present invention, provided is an isolated micro-like RNA (milRNA) selected from:

(i) milRNA with a sequence shown in any of SEQ ID NOs: 1-5 and (ii) milRNA complementary to the nucleotide sequence of milRNA of (i).

In another preferred example, said "complementary" includes "substantially complementary" (the number of non-complementary bases ≤3, preferably ≤3, more preferably ≤1) and "fully complementary".

In another preferred example, said milRNA is from *Salmonella*.

In another preferred example, said milRNA is isolated from blood, body fluids or tissue samples of human or non-human mammals.

In another preferred example, said blood is plasma and/or serum.

In another preferred example, said non-human mammals are mice, rats, rabbits, pigs, cattle, sheep, etc.

In another preferred example, said milRNA is isolated from human.

In the first aspect of the present invention, provided is an isolated or artificially constructed precursor milRNA which can be spliced and expressed as the milRNA of the first aspect of the present invention in animal cells.

In another preferred example, said animal cells include human cells.

In the third aspect of the present invention, provided is an isolated polynucleotide which can be transcribed in an animal cell into a precursor milRNA which can be spliced and expressed as the milRNA of the first aspect of the present invention in a human cell.

In another preferred example, said polynucleotide has the structure of formula I:

$$Seq_{forward}\text{-}X\text{-}Seq_{reverse} \qquad \text{Formula I}$$

In the formula I, $Seq_{forward}$ is a nucleotide sequence which can be expressed as said milRNA in an animal cell;

$Seq_{reverse}$ is a nucleotide sequence substantially complementary or fully complementary to $Seq_{forward}$;

X is a spacer sequence between $Seq_{forward}$ and $Seq_{reverse}$, and said spacer sequence is not complementary to $Seq_{forward}$ and $Seq_{reverse}$;

and after transferred into the animal cell, the structure shown in the formula I forms a secondary structure shown in a formula II:

Formula II

In the formula II, $Seq_{forward}$, $Seq_{reverse}$ and X are defined above,

‖ indicates a complementary base pairing relationship between $Seq_{forward}$ and $Seq_{reverse}$.

In the fourth aspect of the present invention, provided is a vector comprising the milRNA of the first aspect of the present invention, or the polynucleotide of the third or fifth aspect of the present invention.

In the fifth aspect of the present invention, provided is use of the milRNA of the first aspect of the present invention for: (a) the preparation of a reagent, a detecting chip or a kit for detecting *Salmonella* infections; or (b) the preparation of a regulator for regulating the iNOS expression or activity.

In another preferred example, said regulator for regulating iNOS expression or activity is an inhibitor for down-regulating the iNOS expression or activity.

In the sixth aspect of the present invention, provided is a nucleic acid chip, comprising:

a solid-phase carrier; and oligonucleotide probes orderly immobilized on said solid-phase carrier, said oligonucleotide probes specifically capturing the milRNA of the first aspect of the present invention.

In the seventh aspect of the present invention, provided is use of the nucleic acid chip of the sixth aspect of the present invention for the preparation of a kit for detecting *Salmonella* infections.

In the eighth aspect of the present invention, provided is a kit comprising the nucleic acid chip of the sixth aspect of the present invention or the milRNA of the first aspect of the present invention.

In the ninth aspect of the present invention, provided is an inhibitor specifically inhibiting or blocking the milRNA of the first aspect of the present invention.

In another preferred example, said inhibitor is a milRNA sponge, or an antisense nucleic acid or a small molecule compound complementary to the milRNA sequence.

In another preferred example, said inhibitor is a nucleic acid (e.g., RNA, DNA or the like) complementary to the nucleotide sequence of the milRNA of (i) or (ii).

In the tenth aspect of the present invention, provided is the use of the milRNA inhibitor of the ninth aspect of the present invention for the preparation of (a) a medicament for treating *Salmonella* infections, or (b) a medicament for up-regulating the iNOS expression or activity.

In the eleventh aspect of the present invention, provided is a pharmaceutical composition comprising a pharmaceutically acceptable carrier and an inhibitor for specifically inhibiting or blocking the milRNA of the first aspect of the present invention.

In another preferred example, said milRNA inhibitor comprises a milRNA sponge, and an antisense nucleic acid complementary to the sequence of milRNA.

In another preferred example, said milRNA inhibitor is as shown in SEQ ID NO.: 7.

In the twelfth aspect of the present invention, provided is a method for screening medicament candidates for treating *salmonella* infections, comprising the steps of:

(a) providing a test group and a control group, wherein in said test group, a candidate substance is applied to cells or animals of the test group, and the expression level of sal-1 in said test group is detected after the application, and in said control group, the same conditions as the test group are applied, without applying the candidate substance to cells or animals of the control group; and (b) comparing the expression level of sal-1 in the test group with the expression level of sal-1 in the control group;

wherein if the expression level of sal-1 in the test group is significantly lower than the expression level of sal-1 in the control group, it is indicated that this candidate substance is a medicament candidate for treating *Salmonella* infections.

In another preferred example, the sequence of said sal-1 is as shown in SEQ ID NO.: 1.

In another preferred example, said animals include mice, and said cells include the cells cultured in vitro.

In the thirteenth aspect of the present invention, provided is the use of sal-1 for the preparation of a regulator or a pharmaceutical composition for down-regulating the iNOS expression or activity.

In another preferred example, the sequence of said sal-1 is as shown in SEQ ID NO.: 1.

It should be understood that all of the various technical features described above and the various technical features specifically described hereinafter (such as examples) can be combined with one another within the scope of the present invention, so as to form new or preferred technical solutions. Due to space limitations, these are no longer tired out one by one.

DESCRIPTION OF DRAWINGS

FIG. 2 shows electropherograms of ncRNA of the pathogen *Salmonella*. The lanes are as follows:

lane 1 represents a molecular weight standard;

lane 2 represents a sal-1 standard;

lane 3 represents a mock-simulated infection (PBS treated);

lane 4 represents LB-cultured *Salmonella* SE2472 (not in contact with cells); and lane 5 represents *Salmonella* SE2472-infected HT-29 cells;

Particular Embodiments

The present inventor has studied widely and deeply, and is surprised to find that in vivo pathogens (including infectious microorganisms, parasitic microorganisms, symbiotic microorganisms, etc.) will release non-coding RNAs (ncRNAs), and the specific ncRNAs can serve as biomarkers of in vivo pathogens and can be used for effective detection and treatment for in vivo pathogens, thereby significantly improving the diagnosis and treatment of microbial infectious diseases. The present invention is accomplished on this basis.

In particular, the study of the present invention indicates that the in vivo infectious microorganisms, parasitic microorganisms and symbiotic microorganisms may all participate in the physiological homeostasis and the occurrence and progression of diseases by means of ncRNAs. Different pathogens can be detected accurately and rapidly by way of the identification and detection of ncRNAs specific to different pathogens (as biomarkers of the pathogens). Furthermore, based on the ncRNAs produced using host systems by the in vivo pathogens, target inhibition and elimination can be performed such as by the antisense RNA technique, so as to treat microbial infectious diseases. The ncRNA-based therapy provides a new therapeutic strategy for inhibiting microorganisms and/or microbial diseases.

Terminology

As used herein, the terms "milRNA of the present invention" and "*Salmonella* specific milRNA" can be used interchangeably, and indicate any of sal-1, sal-2, sal-3, sal-4 and sal-5 or the combination thereof.

As used herein, the terms "inhibitor", "antagonist" and "blocker" can be used interchangeably and bear the same meaning.

As used herein, the term "sal-1 blocker" refers to a substance capable of inhibiting or blocking the function of sa-1, such as an antisense sequence or a nucleic acid sponge. These inhibitors can inhibit the binding of sal-1 with mRNA of the target gene iNOS and inhibit the down-regulation of sal-1 on the target gene.

Terminology

As used herein, the term "microorganism" includes various tiny organisms, such as viruses, bacteria, archaea, chlamydia, and protists. In this invention, "in vivo microorganism" refers to various microorganisms present in the bodies of hosts (human or other animals), including infectious microorganisms, parasitic microorganisms and symbiotic microorganisms. One typical class of in vivo microorganisms are pathogens causing diseases.

In this invention, according to the relationship between pathogens and host cells, the pathogens can be divided into intracellular bacteria and extracellular bacteria. The extracellular bacteria refer to the bacteria growing and reproducing in the intercellular space, blood, lymph, tissue fluid and other body fluids out of the host cells. The intracellular bacteria are divided into two kinds: facultative intracellular bacteria which are mainly living in cells for growth and reproduction in the host body and can also grow in vitro in a culture medium free of living cells; and obligate intracellular bacteria which have to grow and reproduce in living cells, regardless of in vivo or in vitro.

As used herein, the term "milRNA" is micro-like RNA, referring to the RNA sequence from bacteria and similar to the microRNA.

As used herein, the term "sRNA" is small non-coding RNA, referring to non-coding micro RNA sequence. In this invention, sRNA includes microRNA and milRNA.

iNOS refers to inducible nitric oxide synthase.

Non-Coding RNA

Non-coding RNA (ncRNA) refers to the RNA not translated into proteins, and includes various RNAs, such as rRNA, tRNA, snRNA, snoRNA, and microRNA. These RNAs are transcribed from the genome, are not translated into proteins, participate in the protein translation process, and can exercise their respective biological functions at the RNA level. For example, snRNA and snoRNA participate in the RNA splicing and RNA modification.

The non-coding RNAs are divided in terms of length into three classes: less than 50 nt, including microRNA, siRNA and piRNA; 50 nt to 500 nt, including rRNA, tRNA, snRNA, snoRNA, SLRNA, SRPRNA, etc.; and greater than 500 nt, including long mRNA-like non-coding RNA, long non-coding RNA without a polyA tail, etc.

snRNA is short for small nuclear RNA, and is also called as small nuclear RNA. Its function is to bind with protein factors to form small nuclear ribonucleoprotein particles (snRNPs) to exercise the function of mRNA splicing.

snoRNA is a small RNA first discovered in nucleoli, called as small nucleolar RNA, it was initially discovered that their biological function is to modify the rRNA. Most small nucleolar RNAs can be divided into two classes. One class is C/D box snoRNA, in which some bases of RNA are methylated. The other class is H/ACA box, in which some bases of RNA are modified with methyl uracil, it is characterized by the formation of a double-stem, added with a loop zone in the middle which provided with a box H, there is a box ACA at the tail, and the primary sequence features of box H and box ACA are loosely defined.

miRNA is a small RNA molecule complementary to the transcribed gene to mediate the gene silencing. MicroRNA is a class of 21-23 nt small RNAs, with a precursor of about 70-100 nt, forms a standard stem structure, and is transformed into 21-23 nt single-stranded RNA after processed. The function mechanism of microRNA is to complement the mRNA so as to silence or degrade the mRNA. RNAi technology developed based on the miRNA mechanism is to use small RNA similar to microRNA to silence the corresponding mRNA.

gRNA, also known as guide RNA, refers to the RNA participating in the RNA editing in eucaryotes and having a sequence complementary to the mRNA.

eRNA, an RNA molecule transcribed from an intron or non-coding DNA, can perform fine regulation for the gene transcription and translation efficiency.

Signal recognition particle RNA refers to the RNA functional molecule in cytoplasm for recognizing the mRNA containing signal peptide to determine the secretion.

pRNA refers to bacteriophage RNA. For example, the study shows that, in fi29 bacteriophage, six identical small RNA molecules are used to participate in DNA packaging by using ATP.

tmRNA refers to tRNA-like and mRNA-like complex RNAs. tmRNA is widely present in bacteria to recognize the ribosomes with incorrect translation or code reading, and also to recognize the ribosomes with delay or stalling to mediate disintegration of the ribosomes having problems.

Furthermore, the untranslated region in mRNA, including intron regions and ribosome recognition elements, such as 5'-UTR and 3'-UTR, can also be seen as a non-coding RNA.

milRNA and Precursor Thereof

The present invention provides a novel milRNA from *Salmonella*. Such milRNA is very similar to miRNA, is an RNA molecule, and is obtained by processing a transcript which can form a precursor milRNA. The length generally contains 18-28 nucleotides (nt) (more specifically, about 20-26 nt). Similar to miRNA, milRNA can generally be detected by Northern blotting.

As used herein, "isolated" means that the substance is isolated from its original environment (if it is a natural substance, the original environment is natural environment). For example, polynucleotides and polypeptides in natural state in living cells are not isolated and purified, and when the same polynucleotides or polypeptides are isolated from other substances co-existing in the natural state, they are isolated and purified.

milRNA can be obtained by processing the precursor milRNA (Pre-milRNA), and said precursor milRNA can be folded into a stable stem-loop (hairpin) structure having a general length of 50-100 bp. Said precursor milRNA can be folded into a stable stem-loop structure, and two sides of stem of the stem-loop structure contain two sequences substantially complementary to each other. Said precursor milRNA may be natural or artificially synthetic.

The precursor milRNA can be spliced to generate milRNA, and said milRNA may be substantially complementary to at least a portion of the sequence of the mRNA encoding the gene. As used herein, "substantially complementary" means that the nucleotide sequence is sufficiently complementary and can act upon each other in a predictable manner, e.g., forming a secondary structure (such as a stem-loop structure). Generally, at least 70% of nucleotides in two "substantially complementary" nucleotide sequences are complementary; preferably, at least 80% of nucleotides are complementary; more preferably, at least 90% of nucleotides are complementary; and further preferably, at least 95% of nucleotides are complementary, e.g., 98%, 99% or 100%. Generally, there are at most 40 non-matched nucleotides between two sufficiently complementary molecules; preferably, there are at most 30 non-matched nucleotides; more preferably, there are at most 20 non-matched nucleotides; and further preferably, there are at most 10 non-matched nucleotides, e.g., there are 1, 2, 3, 4, 5 or 8 non-matched nucleotides.

As used herein, the "stem-loop" structure, also known as the "hairpin" structure, refers to a nucleotide molecule which can form a secondary structure comprising a double-stranded region (stem) formed of two regions (on a same molecule) of this nucleotide molecule, the two regions being at two sides of the double-stranded portion; and the structure further comprises at least one "loop" structure, including non-complementary nucleotide molecules, i.e., a single-stranded region. Even if the two regions of the nucleotide molecule are not fully complementary, the double-stranded portion of the nucleotide can also maintain a double-stranded state. For example, insertion, deletion, substitution or the like may lead to a non-complementary small region or make the small region itself form a stem-loop structure or another form of secondary structure. However, the two regions can still be substantially complementary to each other and act upon each other in a predictable manner to form a double-stranded region of the stem-loop structure. The stem-loop structure is well known to a person skilled in the art, and a person skilled in the art could generally determine whether the nucleic acid can form a stem-loop structure after acquiring a nucleic acid having a nucleotide sequence of the primary structure.

The milRNA of the present invention has a sequence shown in SEQ ID NOs: 1-5. To enhance the stability or other properties of milRNA, at least one protective base, such as "TT", can further be added on at least one end of said milRNA.

Antisense Oligonucleotides

According to the milRNA sequence provided in the present invention, the antisense oligonucleotides thereof can be designed. Said antisense oligonucleotides can down-regulate expression of the corresponding milRNA in vivo. As used herein, "antisense oligonucleotides (AS-Ons or ASO)", also known as "antisense nucleotides", refer to DNA molecules or RNA molecules or analogues thereof having a length of about 18-28 nt (more specifically, about 20-26 nt).

In this invention, said "antisense oligonucleotides" further include modified antisense oligonucleotides obtained by locked nucleic acid or nucleic acid chain backbone based modification techniques. Said modification does not substantially alter the activity of antisense oligonucleotides, preferably, said modification can improve the stability, activity or therapeutic effect of antisense oligonucleotides. Locked nucleic acid (LNA) generally refers to a modification technique linking the 2'-oxygen atom with the 4'-carbon atom of ribose through a methylene bridge. LNA can extend the serum half-life of milRNA to improve affinity to the target and reduce the range and extent of off-target effects. Antisense drugs developed by the nucleic acid chain backbone based modification technique are greatly improved in terms of the solubility, resistance to nuclease degradation, etc., and are easy to be synthesized on a large scale. There are many oligonucleotide backbone modification methods, including a thio modification method, e.g., the deoxynucleotide chain is thio modified into a thiodeoxynucleotide chain. In this method, the oxygen atoms of phosphate bonds on the DNA backbone are replaced by sulphur atoms so as to be resistant to nuclease degradation. It should be understood that any modification capable of maintaining most of or all the activity of said antisense oligonucleotides are all included in the present invention.

As a preferred mode of the present invention, the antisense oligonucleotides are subjected to locked nucleic acid modification and more preferably, thio modification.

After transferring the antisense oligonucleotides of the present invention into animal (e.g., a patient with *Salmonella* infection) bodies, they can significantly down-regulate the relevant milRNA expression.

Polynucleotide Constructs

According to the milRNA sequences provided in the present invention, polynucleotide constructs which can be processed, after introduced, into milRNA capable of affecting expression of the corresponding mRNA can be designed, i.e., said polynucleotide constructs can up-regulate the level of the corresponding milRNA in vivo. Therefore, the present invention provides an isolated polynucleotide (construct), said polynucleotide (construct) can be transcribed by human cells into a precursor milRNA which can be spliced and expressed as said milRNA in human cells.

As a preferred mode of the present invention, said polynucleotide construct contains a structure shown in the formula I:

$$Seq_{forward}\text{-}X\text{-}Seq_{reverse} \qquad \text{Formula I}$$

In the formula I, $Seq_{forward}$ is a nucleotide sequence which can be expressed as said milRNA in cells, and $Seq_{reverse}$ is a nucleotide sequence substantially complementary to $Seq_{forward}$; or $Seq_{reverse}$ is a nucleotide sequence which can be expressed as said milRNA in cells, and $Seq_{forward}$ is a nucleotide sequence substantially complementary to $Seq_{reverse}$;

X is a spacer sequence between $Seq_{forward}$ and $Seq_{reverse}$ and said spacer sequence is not complementary to $Seq_{forward}$ and $Seq_{reverse}$;

and after being transferred into cells, the structure shown in the formula I forms a secondary structure shown in a formula II:

Formula II

In the formula II, $Seq_{forward}$, $Seq_{reverse}$ and X are defined above;

|| indicates a complementary base pairing relationship between $Seq_{forward}$ and $Seq_{reverse}$.

Generally, said polynucleotide constructs are located on the expression vector. Therefore, the present invention further comprises a vector containing said milRNA or said polynucleotide constructs. Said expression vector typically further contains a promoter, an origin of replication and/or a marker gene, etc. Methods well known to a person skilled in the art could be used to construct the expression vector required by the present invention. These methods include in vitro recombinant DNA technology, DNA synthesis technology, in vivo recombination technology, etc.

Said expression vector may preferably contain one or more selectable marker genes to provide a phenotypic trait for selection of transformed host cells, such as kanamycin, gentamicin, hygromycin or ampicillin resistance.

Mechanisms

For the convenience of understanding the present invention, the inventor provides the following mechanisms. However, it should be understood that these mechanisms are not used to have any limit to the present invention.

Study of the present invention reveals that after the microorganism infects the human body, some ncRNAs of the microorganism will be secreted and enter the circulatory system, and since these ncRNAs are derived from the microorganism itself, they can be used as a diagnostic marker for the microbial infectious disease.

Typically, ncRNAs present in serum and derived from a microorganism can be used as a diagnostic marker for the microbial infectious disease. These ncRNAs specific to the pathogens in blood or serum can greatly improve the efficiency of diagnosis of the microbial infectious disease, provide great help for the treatment of the disease itself, and has important clinical significance. Moreover, intensive studies on the microorganism-derived ncRNAs will provide new clues for the mechanisms of pathogenesis or infection of such diseases.

Identification Method

The present invention further provides a general method for identifying pathogen-derived ncRNAs.

Taking the identification of ncRNAs of pathogens present in serum or blood as an example, the identification method generally comprises the steps of:

a. collecting blood or serum samples of patients infected with various microorganisms (including bacteria, archaea, viruses, mycoplasma, chlamydia, protists, etc.);

b. primarily screening a group of microorganism-derived sRNAs (including miRNAs) in the patient's blood or serum by means of high-throughput sequencing technology combined with bioinformatics analysis and comparison; and c. further verifying the primarily screened sRNAs using sensitive, accurate real-time fluorescent quantitative PCR to find out the respective specific serum sRNAs, derived from the microorganisms themselves, in serum of patients infected with various microorganisms and evaluate the diagnostic value of the sRNAs for the diseases themselves.

In this invention, for the identified pathogen-derived ncRNAs, feasibility of said ncRNAs as diagnostic markers can be further evaluated.

In this invention, for the identified pathogen-derived ncRNAs, the effect of said ncRNAs in the pathogen infections can be further evaluated.

A typical method is to analyze by in vitro cell infection tests. The method generally comprises the steps of:

a. infecting cells with various microorganisms (including bacteria, archaea, viruses, mycoplasma, chlamydia, protists, etc.), and collecting the infected cell culture fluid;

b. primarily screening a group of microorganism-derived sRNAs (including miRNAs) in the primarily screened cell culture fluid by means of high-throughput sequencing technology (Solexa sequencing technique) combined with bioinformatics analysis and comparison; and c. further verifying the primarily screened sRNAs using sensitive, accurate real-time fluorescent quantitative PCR.

The method described above provided in the present invention can identify and evaluate the specificity and accuracy of one or more ncRNAs (including miRNAs), in the body fluids and blood (or serum) of the patients with microbial infectious diseases and derived from the microorganisms themselves, for the diagnosis of microbial infectious diseases, and compare with the existing clinical diagnostic methods.

Use

Study of the present invention firstly reveals novel means for regulating hosts by in vivo infectious microorganisms, parasitic microorganisms and symbiotic microorganisms. Through the secretory pathway, different in vivo pathogens (such as in vivo infectious microorganisms, parasitic microorganisms and symbiotic microorganisms) present non-coding RNAs (ncRNAs) produced thereby to the host cells, and affect the immune system of the host "by means of" host proteins, thereby helping the in vivo pathogens live in the body of host. Therefore, it is a new way to inhibit microbial infections and treat microbial diseases by interfering with or inhibiting the pathogen-specific ncRNAs.

Based on the present invention, it is found to use a pathogen-specific ncRNA as a detection (or diagnosis) marker and as a therapeutic target.

Taking a *Salmonella* bacterium as example, the *Salmonella* bacterium presents the non-coding RNAs (ncRNAs) encoded by the bacterium itself into a host cell, generates milRNAs similar to microRNAs by means of a microRNA splicing system in the cell, and regulates the immune system (such as iNOS) with milRNAs, which is then utilized by the bacterium so as to protect itself from being cleared by the host. Adsorbing milRNAs using milRNA inhibitors can effectively inhibit the survival ability of the bacterium in the cell, leading to a reduced survival ability of the bacterium, and therefore the inhibitors can be used in the treatment of bacterial infections.

Detection Reagent, Detection Chip and Detection Kit

The present invention further provides a kit for detecting *Salmonella* or *Salmonella* infections, said kit containing the detection reagent or detection chip of the present invention. Said kit can be used to detect expression profiles of the miRNA specific to *Salmonella* infection of the present invention, or used to detect *Salmonella* or *Salmonella* infections. Preferably, said kit further contains a marker for labeling the RNA sample and a substrate corresponding to said marker.

Furthermore, said kit may further comprise various reagents required for extraction of RNA, PCR, hybridization, color development, etc., including but not limited to an extraction buffer, an amplification buffer, a hybridization solution, enzymes, a control solution, a developing solution, a washing liquid, antibodies, etc.

Furthermore, said kit further comprises an instruction and/or a chip image analysis software.

Chip

A microRNA expression profile chip generally contains hundreds, thousands of or more probes, covering a variety of microRNAs, and detects contents of various microRNAs in the sample using the double-stranded homologous complementary principle. Therefore, transcription levels of microRNAs in the sample to be tested can be detected at the same time.

The milRNA sequences of the present invention can also be used to prepare the corresponding milRNA chip and further study the expression profile thereof and the regulation method of milRNAs.

In another aspect, the present invention further provides a chip for analyzing the milRNA expression profile, and said chip can be used to detect *Salmonella* or *Salmonella* infections.

The milRNA chip of the present invention comprises a solid-phase carrier and oligonucleotide probes orderly immobilized on said solid-phase carrier, said oligonucleotide probes comprising nucleic acid sequences related to the sequences shown in SEQ ID NOs: 1-4.

In particular, a suitable probe can be designed according to the milRNA of the present invention and is fixed on the solid-phase carrier to form an "oligonucleotide array". Said "oligonucleotide array" refers to an array having addressable locations (i.e., positions characterized by distinguishing accessible addresses), and each addressable location contains one characteristic oligonucleotide associated therewith. The oligonucleotide array can be divided into a plurality of sub-arrays as desired.

Said solid-phase carrier can use various common materials in the gene chip field, such as but not limited to nylon membranes, active group (such as an aldehyde group and an amino group) modified glass or silicon slices, unmodified glass slices, plastic slices, etc.

Said milRNA chip may be prepared by a conventional method for manufacturing biochips known in the field. For example, if the solid-phase carrier uses a modified glass or silicon slice, and the 5' end of the probe contains an amino-modified poly dT string, the oligonucleotide probes can be prepared into a solution, then the solution is applied to the modified glass or silicon slice using a spotter to arrange in a predetermined sequence or array, and then immobilize by standing overnight, so as to obtain the milRNA chip of the present invention.

The solid-phase hybridization between RNA and milRNA chip of the present invention will be carried out according to the classical method in the art, and a person skilled in the art would readily determine from experience the optimal conditions of buffers, probes, sample concentration, pre-hybridization temperature, hybridization temperature, time, etc. Alternatively, reference can be made to "Molecular Cloning, A Laboratory Manual".

Then the information to be detected is acquired based on the information about locations of marker signals on the milRNA chip, intensity, etc. If the amplified product is labeled with fluorophores, the information to be detected can also be directly obtained by a fluorescent detection device (such as a laser confocal scanner Scanarray 3000).

Pharmaceutical Composition

The present invention further provides a pharmaceutical composition, comprising a pharmaceutically acceptable carrier or an effective amount of an inhibitor, a blocker or an antagonist for the milRNA (e.g., sal-1) of the present invention.

As used herein, the term "effective amount" or "effective dose" refers to the amount that can produce a function or activity to human and/or animals and can also be acceptable to human and/or animals.

As used herein, the "pharmaceutically acceptable" component is applicable to mammals without excessive adverse side effects (such as toxicity, irritation and allergic response), i.e., a substance with a reasonable benefit/risk ratio. The term "pharmaceutically acceptable carrier" refers to a carrier for the administration of a therapeutic agent, including various excipients and diluents.

The pharmaceutical composition of the present invention contains safe and effective amount of the active component of the present invention and a pharmaceutically acceptable carrier. Such carrier includes, but is not limited to, saline, buffer, glucose, water, glycerol, ethanol, and a combination thereof. Generally, a pharmaceutical preparation shall match the mode of administration, and the pharmaceutical composition of the present invention has a dosage form of injection, oral preparation (tablet, capsule, or oral liquid), transdermal agent, or sustained release agent. For example, preparation is performed by a conventional method using physiological saline or an aqueous solution containing glucose and other adjuvants. Said pharmaceutical composition is preferably produced under sterile conditions.

The effective amount of the active component of the present invention may vary depending on the mode of administration and the severity of the disease to be treated. A person skilled in the art could determine the selection of the preferred effective amount depending on various factors (e.g., by clinical trials). Said factors include, but not limited to, the pharmacokinetic parameters of said active component, e.g., bioavailability, metabolism, half-life, etc.; and the severity of the patient's disease to be treated, the patient's weight, the patient's immune state, the administration route, etc. Generally, when the active component of the present invention is administered at a dose of about 0.00001-50 mg/kg body weight (preferably 0.0001-10 mg/kg body weight) per day, satisfactory results can be achieved. For example, due to the urgent requirements of the treatment status, several separate doses can be administered daily, or the dosage is reduced proportionally.

The pharmaceutically acceptable carriers of the present invention include, but not limited to, water, saline, liposomes, lipids, proteins, protein-antibody conjugates, peptides, cellulose, nanogels, or a combination thereof. The choice of carriers should match the mode of administration, which would be well known to a person skilled in the art.

The present invention further provides the use of said pharmaceutical composition for the preparation of a medicament for treating *Salmonella* infections, alleviating the symptoms of *salmonella* infections, reducing the quantity of *Salmonella* in host animals and reducing the mortality of *Salmonella* infections, and for reducing overactive immune responses.

The main advantages of the present invention include:
(a) providing a simple, fast and accurate new method for detecting infections of pathogens (such as *Salmonella*), and
(b) providing a new way to inhibit microbial infections and treat microbial diseases.

The present invention is further illustrated in connection with particular embodiments as follows. It should be understood that these embodiments are merely illustrative of the invention and are not intended to limit the scope of the present invention. For the experimental method with specific conditions being not specified in the following examples, generally conventional conditions are followed, such as the conditions described in Sambrook et al., Molecular Cloning: A Laboratory Manual (New York: Cold Spring Harbour Laboratory Press, 1989), or the conditions recommended by the manufacturer are followed. All percentages and parts are weight percentages and weight parts unless otherwise indicated.

In the following examples, the in vivo pathogen *Salmonella* is studied, the results show that *Salmonella* can produce milRNA (a kind of ncRNA) by making use of the host, and effective detection and treatment for *Salmonella* infections can be performed using the ncRNA.

Example 1

Screening of milRNA in Bacterium Infected Cells

Isolation and streaking for *Salmonella* strains are performed on an LB plate using an inoculating loop, medium-sized colonies are picked and inoculated onto a LB liquid medium, cultured at 37° C. overnight, then centrifuged to remove the LB medium, and the strains are resuspended with RPMI-1640+10% FBS medium.

One day before the infection with bacteria, human intestinal epithelial cells HT-29 digested with trypsin are plated in a cell culture dish, and cultured at 37° C. in a 5% CO2 incubator.

Cells are infected at a ratio of MOI (5-10:1), washed with PBS to remove the bacteria that have not been infected and entered the cells 2 hours after infection, then cultured with gentamicin-containing RPMI-1640+10% FBS, washed with PBS three times after cultured overnight, and cells are lysed with 0.1% PBST (PBS+Triton X-100), and filtered with 0.22 μm filter to remove the bacteria. Through the above treatment, the bacteria that have not entered cells and remain in cells can be completely removed.

Then total RNA is extracted from the lysate with Trizol LS, and subjected to deep sequencing by Solexa, the tested data are analyzed, and *Salmonella* specific small RNA fragments are identified.

1.1 Identification for milRNA

The fragments obtained by Solexa sequencing are analyzed, high-copy milRNA fragment sequences are screened, and quantitative PCR detection probes and northern blot detection probes are designed and synthesized for these sequences.

1.2 Northern Blot Detection

Total RNA of the *Salmonella* strain cultured with LB and cytoplasm total RNA of the cells infected with *salmonella* are extracted respectively with Trizol LS reagent, resuspended with 1×RNA loading buffer (Takara), then subjected to electrophoresis with 15% TBE-Urea polyacrylamide-gelelectrophoresis (PAGE), and the RNAs are transferred and printed on a nylon membrane after electrophoresis, glued by ultraviolet (UV), then hybridized with a digoxin (DIG) labeled probe, and the expression of milRNA is analyzed.

1.3 Fluorescent Quantitative PCR Assay

Total RNA of the *Salmonella* strain cultured with LB and cytoplasm total RNA of the cells infected with *salmonella* are extracted respectively with Trizol LS reagent, then dissolved with ultrapure water treated with DEPC, firstly reverse-transcribed into cDNA with the downstream primer of a probe, then subjected to quantitative PCR amplification with a synthesized probe (ABI), and the content of milRNA in each sample after amplification is analyzed.

Results

Figure 1:
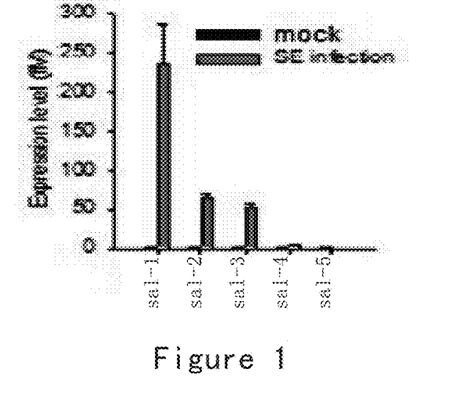
FIG. 1 shows the results of identification for ncRNA of *Salmonella*, an in vivo pathogen. Sals-1, 2, 3, 4, 5 represent different milRNAs detected in the same species of *Salmonella*, and mock means treating with PBS to simulate bacterial infection, so that none of Sals-1, 2, 3, 4, 5 is detected in the cells.
Figure 2:
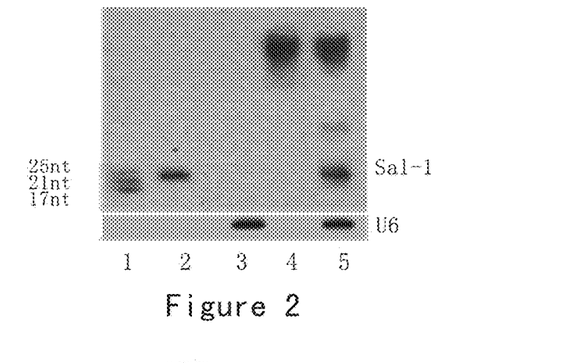
Figure 3:
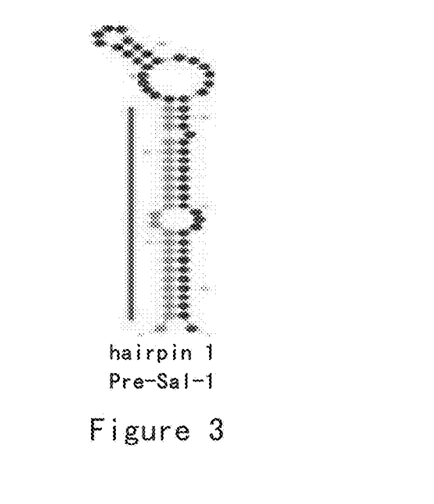
FIG. 3 shows the relationship between *Salmonella* sal-1 and pre-sal-1.

Experimental results are as shown in FIGS. 1, 2 and 3.

Detection is performed using northern blot and qRT-PC, the results of FIGS. 1 and 2 show that small RNAs of 19-30 nt (known as milRNA in the present invention) appear only after the *Salmonella* strain infects cells, and the present invention selects milRNA (sal-1) to make a comprehensive and in-depth study.

The sequence condition of milRNA (sal-1) on the genome of *Salmonella* is analyzed using a biological software, and the detailed results are shown in FIG. 3. FIG. 3 shows that the ncRNA where milRNA (sal-1) is located can be folded into pre-sal-1.

Partial ncRNA sequences from *Salmonella* are as follows:

```
                                          (SEQ ID No.: 1)
Sal-1: UGUGGGCACUCGAAGAUACGGAUU (SEQ ID No.: 2)
Sal-2: AUGCGAGAGUAGGGAACUGCCAGGCAU (SEQ ID No.: 3)
Sal-3: UCCUCUGUAGUUCAGUCGGUAGAACGGC
```

-continued

Sal-4: GAAGGUGGCGGAAUUGGUAGACG (SEQ ID No.: 4)

Sal-5: GCCCGGAUGGUGGAAUCGGUA (SEQ ID No.: 5)

The sequence of Pre-sal-1 is:

(SEQ ID No.: 6)
5'-TGTGGGCACTCGAAGATACGGATTCTTAACGTCCTAGGACGAA
AAATGAATACCAAGTCTCAAGAGTGAACACG-3'

Example 2

The Ability of milRNA Inhibitors to Inhibit the Bacteria Infecting Hosts 2.1 In Vitro Test In this test, for the identified *Salmonella* specific sal-1, the correlation between it and the target gene inducible nitric oxide synthase (iNOS) is studied.

A target site region capable of binding with milRNA is amplified by PCR, double-digested by Spe I+Hind III and inserted into a pMIR-REPORT luciferase vector (purchased from Shanghai Innovation Biotechnology Co., Ltd.) to construct a recombinant plasmid (iNOS). In addition, the milRNA binding site of the above constructed recombinant plasmid is mutated to construct a recombinant mutant plasmid (iNOS mut).

Furthermore, the precursor of milRNA is loaded to an expression vector with CMV as a promoter, to construct a vector (pre-sal-1) overexpressing milRNA.

The milRNA control plasmid or pre-sal-1 and iNOS or iNOS mut are co-transfected into HEK-293T cells, and the reporter gene is detected, with the β-gal plasmid as a reference.

Figure 4:
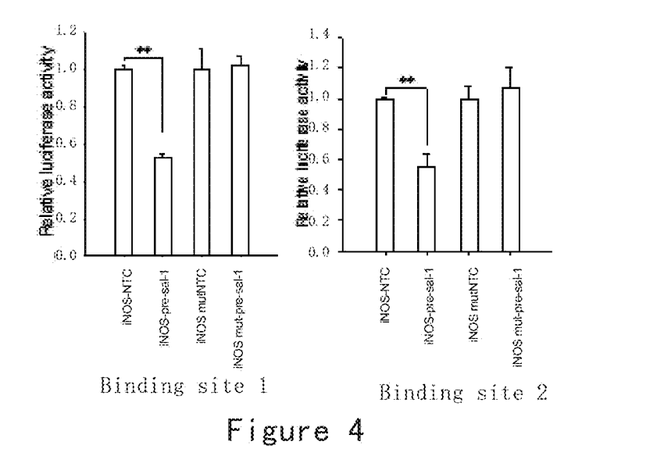
FIG. 4 shows that *Salmonella* sal-1 can regulate two target sites on iNOS.

The particular result is shown in FIG. 4. The result of Luciferase in FIG. 4 shows that sal-1 can regulate both of the two target sites on iNOS, so as to down-regulate iNOS.

2.2 Western Blot

The full-length wild-type iNOS gene is cloned into an eukaryotic expression plasmid to construct a recombinant plasmid expressing iNOS (iNOS WT) for iNOS expression, and furthermore mutation for the milRNA binding sites (synonymous mutation, changing only the base sequence without changing the amino acid sequence) is performed to construct the plasmid expressing iNOS (iNOS MUT) for the expression of mutated iNOS. The pre-sal-1 is co-transfected with iNOS WT and iNOS MUT respectively into mouse RAW264.7 cells (these cells do not express iNOS unless they are stimulated) for expression to detect the regulatory capacity of milRNA on iNOS.

Figure 5:
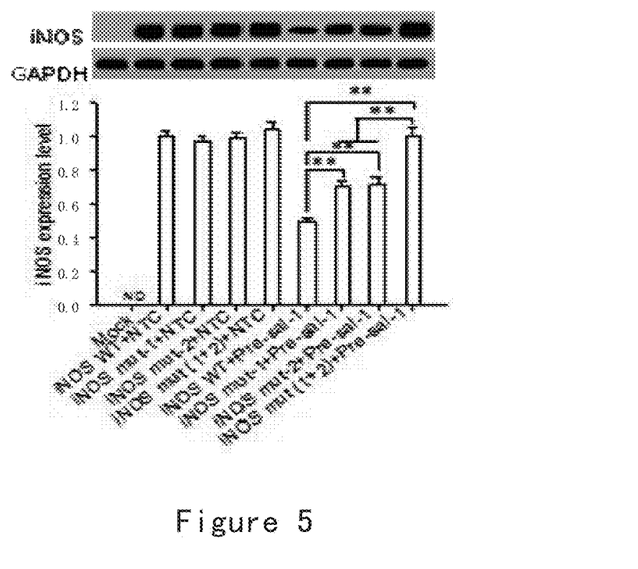
FIG. 5 shows that, after transferring an iNOS full-length expression plasmid into an RAW264.7 cell, sal-1 can likewise successfully regulate the expression of iNOS.

The particular result is shown in FIG. 5. The result in FIG. 5 shows that after transferring iNOS full-length expression plasmids into RAW264.7 cells, sal-1 can likewise successfully regulate the iNOS expression (down-regulation).

2.3 Cell Infection Test

HT-29 cells are plated in a 24-well plate one day before infected with a *Salmonella* strain, and on the next day transfected with anti-sal-1 using lipofectin 2000, and in 24 h after transfection with anti-sal-1, the cells are infected with the *Salmonella* strain in an MOI (5-10:1) with the control group using random sequences, and the survival ability of intracellular bacteria is detected in 24 h after infection.

Figure 6:
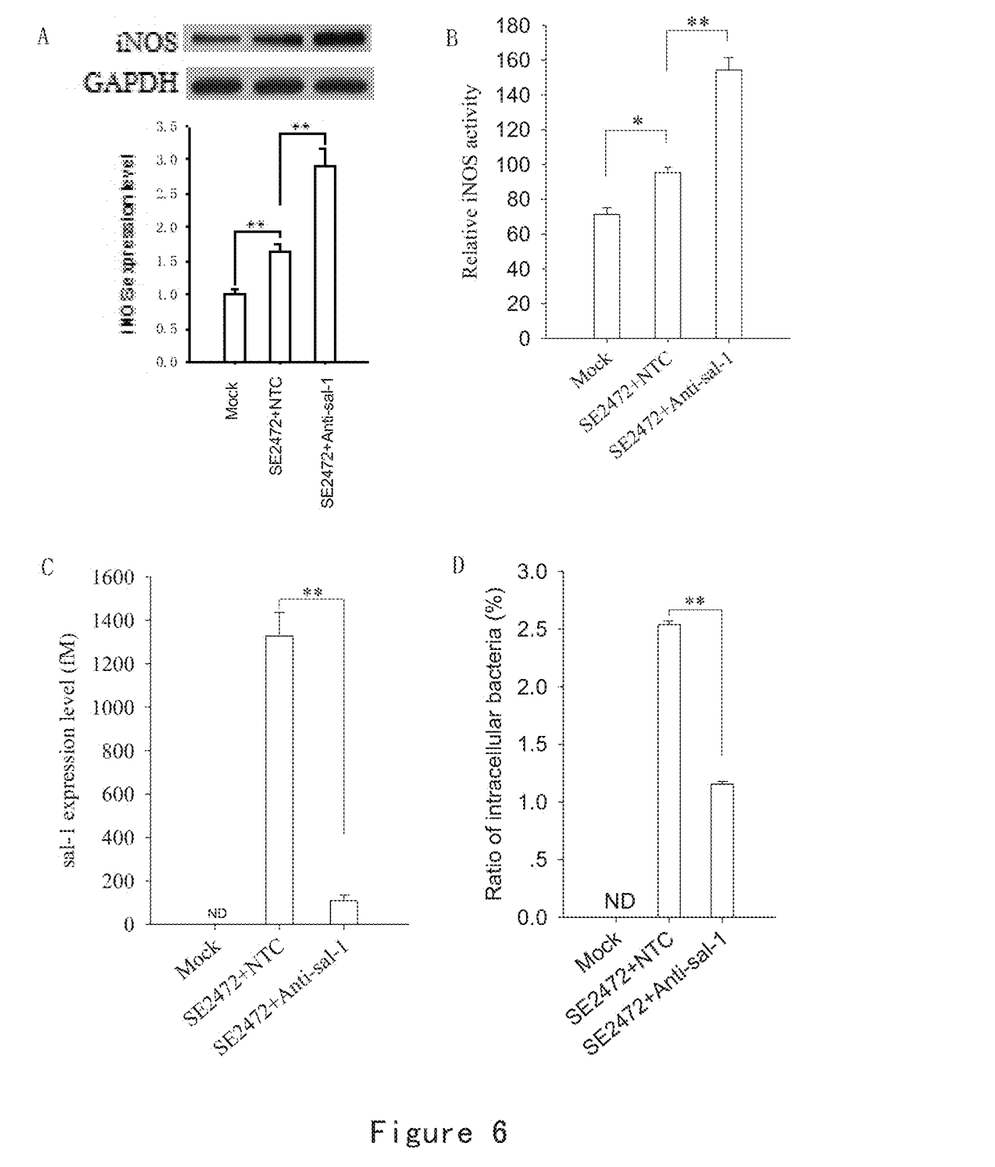
FIG. 6 shows the regulation of *Salmonella* milRNA (sal-1) for the target gene iNOS.

The antisense nucleic acids have sequences (5' to 3') as follows:

(SEQ ID NO.: 7)
anti-sal-1: AAUCCGUAUCUUCGAGUGCCCACA (SEQ ID NO.: 8)
anti-sal-2: AUGCCUGGCAGUUCCCUACUCUCGCAU (SEQ ID NO.: 9)
anti-sal-3: GCCGUUCUACCGACUGAACUACAGAGGA (SEQ ID NO.: 10)
anti-sal-4: CGUCUACCAAUUCCGCCACCUUC (SEQ ID NO.: 11)
anti-sal-5: UACCGAUUCCACCAUCCGGGC The detailed results are shown in FIG. 6. FIG. 6 shows that, with human intestinal epithelial cells (HT-29) as a model of infection, when the HT-29 cells are infected with a *Salmonella* strain, the cells are transfected with the sal-1 inhibitor (anti-sal-1), then the expression of iNOS is analyzed and activity detection is performed, and the survival rate of the *Salmonella* strain in cells is analyzed. The iNOS expression of the *Salmonella* strain infected with the sal-1 inhibitor is further increased by about 2.8-fold (FIG. 6A); and the iNOS activity is also increased accordingly by about 2.3-fold (FIG. 6B). However, the sal-1 expression level is down-regulated by about 90% (FIG. 6C), and the number of *Salmonella* in cells after the infection is also decreased to 45% (FIG. 6D).

2.4 In Vivo Experiment

The pre-sal-1 sequence after enzyme digestion is inserted into a conventional lentivirus vector to package the lentivirus overexpressing milRNA.

The sequence complementarily binding with milRNA is constructed into a sponge capable of binding with milRNA (containing 3 repetitions of complementary fragment) by means of genetic engineering, and then the milRNA sponge is also inserted into the lentivirus vector to package the lentivirus capable of adsorbing milRNA.

In addition, since iNOS can also be expressed in a body of mouse, in order to verify the regulatory function of milRNA on iNOS, the present inventor constructs an expression plasmid with all the binding sites of milRNA on mouse iNOS being mutated, then this plasmid is also enzymatically digested and then inserted into the lentivirus vector to package the lentivirus capable of overexpressing the mouse iNOS.

Taking 6-8 weeks old BALA/C mice as experimental subjects, the effect of the up- or down-regulation of milRNA on the expression of iNOS is analyzed, and the invasion in mice is compared. Taking 6-8 weeks female BALB/C mice as infection models, the lentivirus overexpressing milRNA (sal-1), the lentivirus overexpressing iNOS (the sal-1 binding site of mouse iNOS is subjected to the amino acid synonymous mutation to result in a capacity of not binding or lowly binding with sal-1), and the lentivirus specifically adsorbing milRNA (sal-1) sponge, are packaged using recombinant lentivirus respectively. The experiment is divided into 8 groups: mock; *Salmonella* (SE2472); lenti-NTC+SE2472; lenti-sal-1+SE 2472; lenti-sal-1 sponge+SE2472; lenti-NTC+iNOS MUT SE2472; lenti-sal-1+iNOS MUT SE2472; and lenti-sal-1 sponge+iNOS MUT SE2472.

Figure 7:
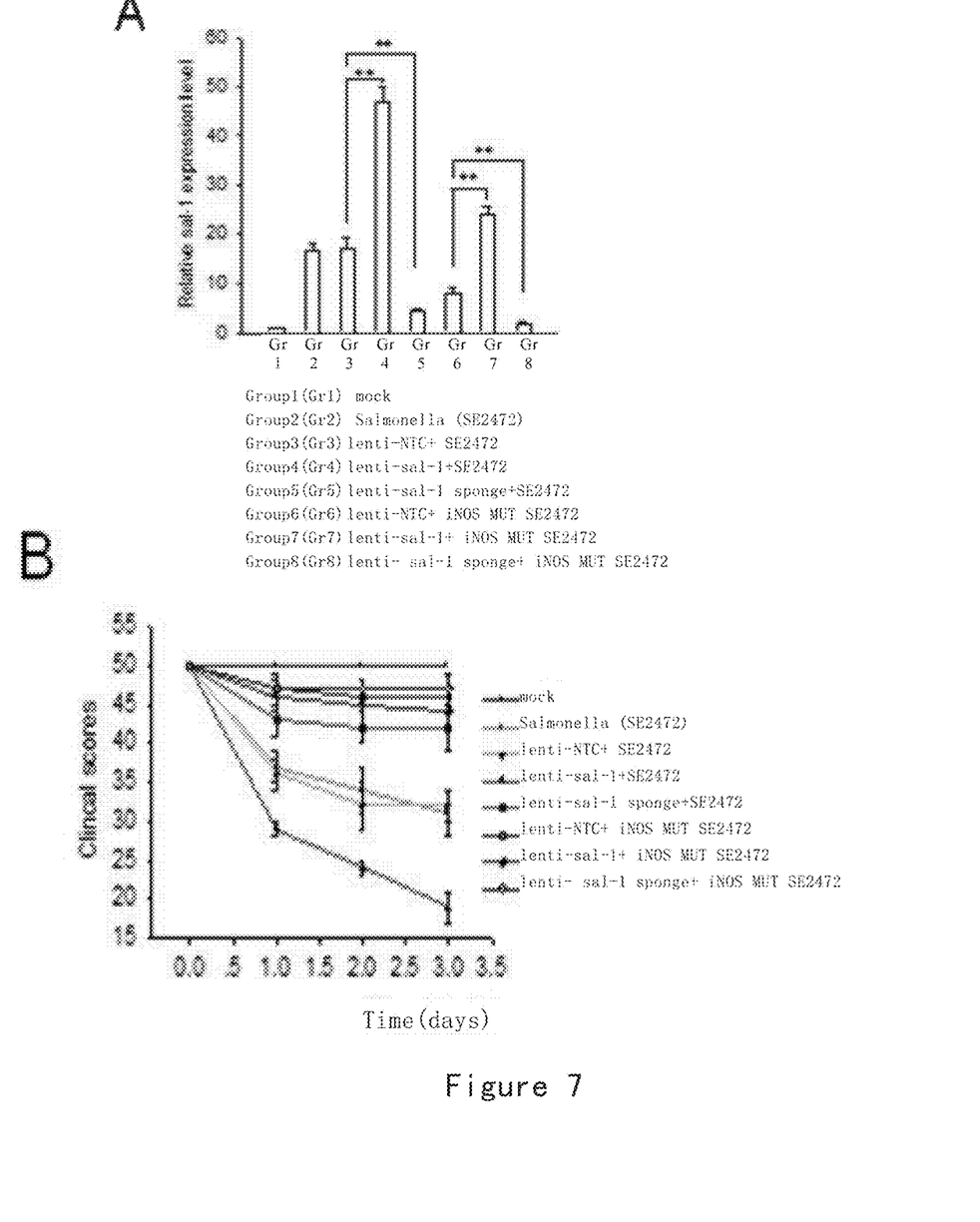
FIG. 7 shows the regulation effect of Sal-1 in *Salmonella* infected mice.

The detailed results are shown in FIG. 7. FIG. 7 shows the expression of sal-1 in the mouse model.

The result of FIG. 7A shows that, after the mice are infected with *Salmonella* SE2472, the expression of sal-1 is increased, the expression of sal-1 in the group lenti-sal-1+ SE2472 is further increased, and the expression level of sal-1 in the group lenti-sal-1 sponge+SE2472 is decreased due to the adsorption by the sal-1 sponge (an inhibitor for sal-1). When the sal-1 binding sites of iNOS in mice are subjected to synonymous mutation and then packaged into lentivirus to re-infect the mice, the sal-1 is decreased (because the expression of mutant iNOS affects the survival ability of bacteria in mice, and the number is decreased), and the expression of sal-1 in the group lenti-sal-1+iNOS MUT SE2472 shows a certain scale of response expression, while the expression of sal-1 in the group lenti-sal-1 sponge+iNOS MUT SE2472 is further decreased.

FIG. 7B indicates that the eight groups of mice have changed clinical symptoms when infected with SE2472, and these changes are consistent with the changes in bacterial infection symptoms caused by the above changes of sal-1.

FIGS. 7C and 7D show the change in expression of iNOS in the eight groups, wherein in the *Salmonella* SE2472 infection, the expression difference of iNOS is not significant, and only when the sal-1 sponge is used, the expression of iNOS can obviously achieve a response expression. This clearly indicates that sal-1 regulates the expression of iNOS, and when iNOS is subjected to synonymous mutation, it can be seen that the expression of iNOS is further increased, and is not regulated by sal-1. The results show that sal-1 can indeed regulate the expression of iNOS.

In FIG. 7E, the bacterial contents in the tissues (*Salmonella* removed from the enteric cavity) of large intestines of mice in the eight groups are detected. The up-regulated expression of sal-1 can promote the infection ability of bacteria in the intestinal tissue, and after the sal-1 is adsorbed and removed by the sponge, the infection ability of bacteria are decreased. In the iNOS synonymous mutation group, sal-1 does not play a regulatory role. All the results indicate that sal-1 regulates iNOS, and affects the infection and survival ability of the bacteria in the body of host through iNOS.

The result of the example of the present invention indicates that the *Salmonella* bacterium presents the non-coding RNAs (ncRNAs) encoded by the bacterium itself into a host cell, generates milRNAs similar to microRNAs by means of a microRNA splicing system in the cell, and regulates the immune system (such as iNOS) with milRNAs, which is then utilized by the bacterium so as to protect itself from being cleared by the host. In the present invention, the milRNA inhibitor can effectively inhibit the survival ability of the bacteria in cells through adsorbing milRNA, leading to a reduced survival ability of *Salmonella*, therefore the inhibitor can be used in the treatment of bacterial infections.

Example 3

Use of *Salmonella* milRNA

The milRNA of the present invention is used for (a) the preparation of a reagent, a detecting chip or a kit for detecting *Salmonella* infections; or (b) the preparation of a regulator for regulating the iNOS expression or activity The nucleic acid chip for detecting *Salmonella* infections comprises: a solid-phase carrier; and oligonucleotide probes orderly fixed on the said solid-phase carrier, and the said oligonucleotide probes specifically capture the milRNA of the present invention.

The nucleic acid chip for detecting *Salmonella* infections of the present invention can screen with a high-throughput milRNA probes that stably change in serum, and furthermore predict and diagnose diseases through the overall change of milRNA in serum. The inventor firstly determines milRNA with no less than one copy in serum by the sequencing or quantitative PCR method, then synthesize reverse complementary probes of these milRNAs, and then spot these probes on a 75×25 mm chemically modified glass slide by a chip spotter SmartArray™. The samples spotted to the chip further include U6 as an interior label, tRNA, an artificially prepared external label with 30-base length, a positive control Hex, etc. The whole dot array is divided into four sub-arrays, each of which has 23 rows and 21 columns, with dot interval of 185 µm and dot diameter of about 130 µm, and each probe is replicated three times.

The chip operation process is as follows: (1) extraction of total RNA from serum/plasma, and detection of the mass of total RNA by formaldehyde denaturing gel electrophoresis; (2) isolation of milRNA: taking 50-100 µg of total RNA, and isolating milRNA with Ambion's miRNA Isolation Kit (Cat #. 1560); (3) fluorescence labelling of milRNA samples: performing fluorescence labelling with T4 RNA ligase labelling method, then precipitating with absolute ethyl alcohol, and blow-drying for chip hybridization; (4) hybridization and washing: dissolving the RNA in a 16 µL hybridization solution (15% formamide; 0.2% SDS; 3×SSC; and 50×Denhardt's solution), and hybridizing overnight at 42° C., and after hybridization, washing in a liquid containing 0.2% SDS and 2×SSC at about 42° C. for 4 minutes, then washing in 0.2×SSC at room temperature for 4 minutes, and drying the glass slide for scanning; (5) chip scanning: scanning the chip using a LuxScan 10K/A dual-channel laser scanner; and (6) data extraction and analysis: analyzing the chip image using a LuxScan 3.0 image analysis software, converting the image signals into digital signals, and finally choosing differentially expressed genes by SAM analysis.

The serum/plasma milRNA probes that show a large extent of differential expressions between *Salmonella* infections and under the normal physiological state by verification with both quantitative PCR technology and biochip technology can be used for the preparation of biochips, and the method is the same as above. Being compared with traditional chips, this chip has no significant improvement on the manufacture process and operation procedure, but it simplifies the probe library, which will greatly reduce the production cost and time, and can be easily prepared. It also increases the specificity and practicability of the chip. When this chip is put into practice, it can detect diseases at an early stage and help guide diagnosis and treatment, which only needs the patient's serum/plasma without any other tissue.

In addition, the nucleic acid chip of the present invention is used to prepare a kit for detecting *Salmonella* infections. The kit for detecting *Salmonella* infections contains the nucleic acid chip of the present invention or the milRNA of the present invention.

The production process and operation procedure of the milRNA kit for the diagnosis and efficacy evaluation for *Salmonella* infections as well as the screening and efficacy evaluation of pharmaceutically active ingredients are based on quantitative and semi-quantitative PCR technology and biochip technology.

Firstly, milRNAs with no less than one copy in serum are determined by the sequencing or quantitative PCR method. Then the serum/plasma milRNAs that show significant expression differences between under a diseased state and normal physiological state are screened by quantitative PCR technology and biochip technology, as an indicator for predicting whether a *Salmonella* infection occurs and diagnosing the disease degree. Finally, the number of corresponding serum/plasma milRNAs is screened, and this is the optimized simplification made on the basis of the chip probe library. This kit comprises serum/plasma milRNA primers, Taq polymerase, dNTP and other reagents. The value of this kit is that, it only needs serum/plasma without other tissue samples, and can be used to detect the change trend of milRNA with the simplest probe library and then the likelihood of *Salmonella* infection occurrence can be predicted or the pathologic stages of *Salmonella* infections can be diagnosed according to this change trend. Therefore, this kit can be put into practice to increase the possibility of detecting *Salmonella* infections at an early stage to help guide diagnosis and treatment.

All the documents referred to in the present invention are incorporated by reference as if each reference cited as alone as a reference in the present application. In addition, it should be understood that after reading the teachings of the present invention described above, a skilled in the art can make various changes or modifications of the invention, and these equivalent forms also fall into the scope as defined by the appended claims of the present application.

The invention claimed is:

1. An artificially constructed precursor milRNA, wherein the artificially constructed precursor milRNA is spliced and expressed in an animal cell into a milRNA having the nucleotide sequence set forth in SEQ ID NO:1, or a milRNA complementary to the nucleotide sequence set forth in SEQ ID NO:1.

2. A polynucleotide which is transcribed in an animal cell into an artificial precursor milRNA, wherein the artificial precursor milRNA is spliced and expressed in an animal cell into a milRNA having the nucleotide sequence set forth in SEQ ID NO:1, or a milRNA complementary to the nucleotide sequence set forth in SEQ ID NO:1.

3. A vector, wherein the said vector contains a milRNA having the nucleotide sequence set forth in SEQ ID NO:1, or a milRNA complementary to the nucleotide sequence set forth in SEQ ID NO:1.

4. A vector, wherein the said vector contains the polynucleotide of claim 2.

* * * * *